(12) United States Patent
Dorawa et al.

(10) Patent No.: US 9,402,651 B2
(45) Date of Patent: Aug. 2, 2016

(54) FIXATION CLAMP

(71) Applicant: Stryker Trauma SA, Selzach (CH)

(72) Inventors: Klaus Dorawa, Schoenkirchen (DE); Adam Busch, Olten (CH); Claudio Küng, Zollikofen (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 66 days.

(21) Appl. No.: 14/444,181

(22) Filed: Jul. 28, 2014

(65) Prior Publication Data

US 2014/0336649 A1   Nov. 13, 2014

Related U.S. Application Data

(63) Continuation of application No. 13/302,559, filed on Nov. 22, 2011, now Pat. No. 8,827,998.

(30) Foreign Application Priority Data

Dec. 14, 2010 (EP) .................................... 10194945

(51) Int. Cl.
*A61B 17/64* (2006.01)

(52) U.S. Cl.
CPC ........... *A61B 17/6466* (2013.01); *A61B 17/645* (2013.01); *A61B 17/6416* (2013.01); *A61B 17/6458* (2013.01)

(58) Field of Classification Search
CPC combination set(s) only.
See application file for complete search history.

(56) References Cited

U.S. PATENT DOCUMENTS

| | | |
|---|---|---|
| 2,250,417 A | 7/1941 | Ettinger |
| D228,970 S | 10/1973 | Cohen |
| D237,631 S | 11/1975 | Katzman |
| 4,008,720 A | 2/1977 | Brinckmann et al. |
| D255,713 S | 7/1980 | Sturges |
| 4,252,121 A | 2/1981 | Arnegger |
| D282,962 S | 3/1986 | Gerber |
| D283,725 S | 5/1986 | Mahoney |

(Continued)

FOREIGN PATENT DOCUMENTS

| | | |
|---|---|---|
| CH | 657899 A5 | 9/1986 |
| DE | 518329 C | 2/1931 |

(Continued)

OTHER PUBLICATIONS

European Search Report for EP 10194945.1 dated Feb. 25, 2011.

(Continued)

*Primary Examiner* — Jan Christopher Merene
(74) *Attorney, Agent, or Firm* — Lerner, David, Littenberg, Krumholz & Mentlik, LLP

(57) ABSTRACT

A fixation clamp for use in an external fixation system for holding bone fragments adjacent to each other with the help of fixation elements, has of at least one clamping assembly having at least one reception provided by means of grooves to accommodate a fixation element along the longitudinal axis of the reception. At least one locking element extends through the clamping assemblies for blocking the position of the clamping assemblies in a defined angular position. The clamping assembly comprises a first jaw and a second jaw which are in contact with each other via respective contact surfaces. The clamping assembly comprises at least two orientation devices that extend from and/or into said contact surfaces which at least two orientation devices serve to orient the first jaw with respect to the second jaw.

15 Claims, 8 Drawing Sheets

(56) References Cited

U.S. PATENT DOCUMENTS

| | | | |
|---|---|---|---|
| 4,620,533 A | 11/1986 | Mears | |
| 4,662,365 A | 5/1987 | Gotzen et al. | |
| D301,496 S | 6/1989 | Yonesawa et al. | |
| 5,071,437 A | 12/1991 | Steffee | |
| 5,098,432 A | 3/1992 | Wagenknecht | |
| 5,152,280 A | 10/1992 | Danieli | |
| 5,304,177 A | 4/1994 | Pennig | |
| 5,376,091 A | 12/1994 | Hotchkiss et al. | |
| 5,429,637 A | 7/1995 | Hardy | |
| 5,443,465 A | 8/1995 | Pennig | |
| 5,630,815 A | 5/1997 | Pohl et al. | |
| D380,262 S | 6/1997 | Van Funderburk et al. | |
| 5,662,648 A | 9/1997 | Faccioli et al. | |
| 5,746,741 A | 5/1998 | Kraus et al. | |
| 5,752,954 A | 5/1998 | Mata et al. | |
| 5,827,282 A | 10/1998 | Pennig | |
| 5,846,245 A | 12/1998 | McCarthy et al. | |
| 5,891,144 A | 4/1999 | Mata et al. | |
| 5,921,985 A | 7/1999 | Ross, Jr. et al. | |
| 6,019,769 A | 2/2000 | McCarthy et al. | |
| 6,024,745 A | 2/2000 | Faccioli et al. | |
| 6,080,153 A | 6/2000 | Mata et al. | |
| D429,334 S | 8/2000 | Solem | |
| 6,217,577 B1 | 4/2001 | Hofmann | |
| 6,308,598 B1 | 10/2001 | O'Neil | |
| D455,831 S | 4/2002 | Koros et al. | |
| 6,386,786 B1 | 5/2002 | Perlman et al. | |
| 6,409,729 B1 | 6/2002 | Martinelli et al. | |
| 6,482,206 B2 | 11/2002 | Schoenefeld | |
| 6,520,962 B1 | 2/2003 | Taylor et al. | |
| 6,565,564 B2 | 5/2003 | Hoffman et al. | |
| 6,613,049 B2 | 9/2003 | Winquist et al. | |
| 6,616,664 B2 | 9/2003 | Walulik et al. | |
| 6,652,523 B1 | 11/2003 | Evrard et al. | |
| D483,642 S | 12/2003 | Lin | |
| 6,702,814 B2 | 3/2004 | Walulik et al. | |
| D493,225 S | 7/2004 | Varga et al. | |
| D494,274 S | 8/2004 | Varga et al. | |
| D501,555 S | 2/2005 | Varga et al. | |
| 6,916,319 B2 | 7/2005 | Munting | |
| 7,004,943 B2 | 2/2006 | Ferrante et al. | |
| 7,048,735 B2 | 5/2006 | Ferrante et al. | |
| D526,410 S | 8/2006 | Phillips et al. | |
| D532,277 S | 11/2006 | Shih | |
| D537,939 S | 3/2007 | Phillips et al. | |
| 7,261,713 B2 | 8/2007 | Langmaid et al. | |
| D551,763 S | 9/2007 | Phillips et al. | |
| 7,282,052 B2 | 10/2007 | Mullaney | |
| D556,899 S | 12/2007 | Veliss et al. | |
| D558,337 S | 12/2007 | Jones et al. | |
| 7,449,023 B2 | 11/2008 | Walulik et al. | |
| 7,479,142 B2 | 1/2009 | Weiner et al. | |
| 7,491,008 B2 | 2/2009 | Thomke et al. | |
| 7,527,626 B2 | 5/2009 | Lutz et al. | |
| 7,562,855 B2 | 7/2009 | Oetlinger | |
| 7,588,571 B2 | 9/2009 | Olsen | |
| 7,608,076 B2 | 10/2009 | Ezzedine | |
| 7,618,417 B2 | 11/2009 | Thomke et al. | |
| D607,102 S | 12/2009 | Robinson | |
| 7,749,224 B2 | 7/2010 | Cresina et al. | |
| 7,806,623 B2 | 10/2010 | Thomke et al. | |
| D632,791 S | 2/2011 | Murner | |
| D633,206 S | 2/2011 | Murner | |
| D633,207 S | 2/2011 | Murner | |
| D633,208 S | 2/2011 | Murner | |
| 8,172,840 B2 | 5/2012 | Murner et al. | |
| D663,030 S | 7/2012 | Murner et al. | |
| 8,388,619 B2 | 3/2013 | Mullaney | |
| 8,827,997 B2 * | 9/2014 | Cremer | A61B 17/6466 606/324 |
| 2001/0049526 A1 | 12/2001 | Venturini et al. | |
| 2002/0037193 A1 | 3/2002 | Gibbons et al. | |
| 2002/0077629 A1 | 6/2002 | Hoffman et al. | |
| 2003/0199738 A1 | 10/2003 | Yager | |
| 2004/0044344 A1 | 3/2004 | Winquist et al. | |
| 2004/0059331 A1 | 3/2004 | Mullaney | |
| 2005/0203520 A1 | 9/2005 | Volzow | |
| 2005/0240265 A1 | 10/2005 | Kuiper et al. | |
| 2006/0025703 A1 | 2/2006 | Miles et al. | |
| 2006/0039750 A1 | 2/2006 | Thomke et al. | |
| 2006/0052785 A1 | 3/2006 | Augostino et al. | |
| 2006/0155276 A1 | 7/2006 | Walulik et al. | |
| 2006/0167453 A1 | 7/2006 | Hoffmann-Clair et al. | |
| 2006/0287652 A1 | 12/2006 | Lessig et al. | |
| 2007/0038217 A1 | 2/2007 | Brown et al. | |
| 2007/0123856 A1 | 5/2007 | Deffenbaugh et al. | |
| 2007/0198012 A1 | 8/2007 | Thomke et al. | |
| 2007/0233061 A1 | 10/2007 | Lehmann et al. | |
| 2008/0065068 A1 | 3/2008 | Thomke et al. | |
| 2008/0215053 A1 | 9/2008 | Thomke et al. | |
| 2008/0306527 A1 | 12/2008 | Winslow et al. | |
| 2008/0306528 A1 | 12/2008 | Winslow et al. | |
| 2009/0018541 A1 | 1/2009 | Lavi | |
| 2009/0088751 A1 | 4/2009 | Mullaney | |
| 2009/0099565 A1 | 4/2009 | Weiner et al. | |
| 2009/0299368 A1 | 12/2009 | Bauer | |
| 2009/0306661 A1 | 12/2009 | Thomke et al. | |
| 2009/0326532 A1 | 12/2009 | Schulze | |
| 2010/0298827 A1 | 11/2010 | Cremer et al. | |
| 2011/0066151 A1 | 3/2011 | Murner et al. | |
| 2011/0087226 A1 | 4/2011 | Murner et al. | |
| 2012/0004659 A1 | 1/2012 | Miller et al. | |
| 2012/0150180 A1 * | 6/2012 | Verma | A61B 17/6416 606/59 |
| 2012/0150181 A1 | 6/2012 | Dorawa et al. | |
| 2012/0150182 A1 | 6/2012 | Dominik et al. | |
| 2012/0150183 A1 | 6/2012 | Dorawa et al. | |
| 2015/0119886 A1 * | 4/2015 | Milella, Jr. | A61B 17/6466 606/59 |

FOREIGN PATENT DOCUMENTS

| | | |
|---|---|---|
| DE | 10246418 A1 | 4/2004 |
| EP | 314021 A2 | 5/1989 |
| EP | 0700664 A1 | 3/1996 |
| EP | 2250968 A1 | 11/2010 |
| FR | 2787697 A1 | 6/2000 |
| JP | 2003325058 A | 11/2003 |
| WO | 0156486 A1 | 8/2001 |
| WO | 2006116307 | 11/2006 |
| WO | 2007001945 A1 | 1/2007 |

OTHER PUBLICATIONS

European Search report for EP 10194944.4 dated Feb. 23, 2011.
http://www.smith-nephew.com/us/professional/products/all-products/jet-x/ searched RMS Jan. 15, 2013.
http://emedicine.medscape.com/article/1982756-overview searched RMS Jan. 15, 2013.
Extended European Search Report for Application No. 10194943.6 dated Feb. 23, 2011.

* cited by examiner

FIXATION CLAMP

CROSS-REFERENCE TO RELATED APPLICATION

The present application is a continuation of U.S. patent application Ser. No. 13/302,559, filed Nov. 22, 2011, which issued as U.S. Pat. No. 8,827,998 on Sep. 9, 2014, and claims priority from European Patent Application No. 10 194 945.1, filed Dec. 14, 2010, the disclosures of which are hereby incorporated herein by reference.

BACKGROUND OF THE INVENTION

The present invention relates to a fixation clamp and, more particularly, to a fixation clamp for use in an external fixation system for holding bone fragments adjacent each other. External fixation systems are widely used to connect two or more bone fragments to each other. Such systems comprise bone screws, pins, wires which are inserted directly into the bone material and these systems use external structural elements as fixation rods, bars and rings. In order to connect the rods and bars to form a rigid frame, fixation clamps are used. Furthermore, fixation clamps are used to connect the screws and pins to the rigid frame to specifically hold bone fragments at an intended place.

One adjustable fixation clamp is known from U.S. Pat. No. 6,080,153 comprising two pairs of jaws allowing clamping of a rod as well as of a pin.

A clamp for multiple rod-shaped elements is known from U.S. Pat. No. 7,618,417 having one single pair of jaws. However, such a clamp allows clamping more than two, e.g. three or four rod-shaped elements as pins with one single clamp, thus reducing the number of clamps. However, one further fixation clamp is necessary to fix the rod of said clamp to the frame of the fixation system.

U.S. Patent Application Publication No. 2006/0287652 mentions that usual fixation clamps as e.g. known from U.S. Pat. No. 6,080,153 allow clamping of one single screw or pin to the frame. This way of attaching pins or rods leads to bulky fixation systems. Therefore 2006/0287652 discloses a fixation clamp addressing this problem and comprises two pairs of jaws within which each pair of jaws allows the introduction and clamping of two rods or pins etc. at the same time.

These clamps according to the prior art either provide different diameters of the reception openings provided by the jaws to introduce different sizes of rods, pins or wires, or they rely on additional inserts as e.g. disclosed in U.S. Publication 2008/0065068. Such inserts reduce the diameter of the reception cavities to allow a secure fixing of differently sized rods, pins or wires.

From U.S. Publication 2010/0298827 a further fixation clamp is known. The disclosure of U.S. 2010/0298827 is incorporated herein by reference. Users feel very comfortable with the fixation clamp according to this design. However, past use has shown that in some applications the jaws of the clamping assembly have been orientated in an erroneous manner which led to unsatisfactory results. Hence there is a need to have a fixation clamp with which erroneous alignment of the jaws is prevented.

SUMMARY OF THE INVENTION

It is one aspect of the present invention to provide a fixation clamp which overcomes the disadvantages of prior art. It is in particular one aspect of the present invention to provide a fixation clamp with which erroneous alignment of the jaws is prevented. Furthermore such a fixation clamp shall be adjustable during the mounting process to a large degree.

Such an aspect is achieved by the features of claim 1. Accordingly a fixation clamp, more particularly for use in an external fixation system for holding bone fragments adjacent to each other with the help of fixation elements, comprises at least one clamping assembly having at least one reception provided by means of grooves to accommodate a fixation element along the longitudinal axis of the reception. At least one locking element extends through the clamping assemblies for blocking the position of the clamping assemblies in a defined angular position. This clamping assembly comprises a first jaw and a second jaw which are in contact with each other via respective contact surfaces. The clamping assembly comprises at least two, preferably exactly two, orientation devices that extend from and/or into the contact surfaces which at least two orientation devices serve to orient the first jaw with respect to the second jaw.

The arrangement of at least two orientation devices has the advantage that a misalignment of the jaws can be prevented. Furthermore the jaws will be positioned with an enhanced accuracy. In case the clamping assembly is designed such that a pivoting motion between the clamping assembly and the locking element becomes possible, the arrangement of the at least two orientation devices is also very advantageous to compensate possible misalignments during the mounting process.

The orientation device comprises preferably an opening extending from said surface into the respective jaw and a protrusion extending from said surface away from the respective jaw wherein said protrusion engages in the opening. Hence one of the jaws comprises the openings and the other jaw comprises the protrusions. Alternatively it is also possible to mix the openings with the protrusion on one of the jaws, namely to arrange a protrusion and an opening on a first jaw and an opening and a protrusion on a second jaw.

The openings have preferably the shape of a channel or slot extending along an axis which is substantially parallel to the plane of the surface. The slot or channel has the advantage that the width of the slot or channel can be varied for several purposes.

Preferably the protrusions extend in direction of the central axis of the locking element and the axis of the channel extends substantially perpendicular to the central axis, wherein the protrusion engages into the channel perpendicular to the axis of the channel.

Preferably the channel opens out into neighboring grooves. Thereby the channel is accessible from two sides which is advantageous for cleaning purposes. In this case the sidewalls of the channels serves as abutment element for the protrusion. Hence the protrusion engages with the sidewalls of the channels.

Alternatively the channel can also be limited on the opposite side of one of the grooves as viewed along the respective axis of the channel by an abutment element, which abutment element has a surface which is preferably curved around a central axis extending perpendicular to the respective surface. Here the abutment element as well as partly the sidewalls serve as abutment element for the protrusion.

A first channel extends preferably along a first axis being parallel to the surface and a second channel extends along a second axis being parallel to the surface, wherein the first axis is angularly arranged to the second axis.

The protrusions have preferably the shape of pins preferably with a circular cross-section. The protrusions and the openings are arranged such that the first jaw and the second jaw are connectable in only one determined aligned position.

Preferably the orientation devices are provided such that rotation of the first jaw with respect to the second jaw is prevented. Alternatively the orientation devices are provided such that rotation of the first jaw with respect to the second jaw is permitted in a narrow field of rotation such as rotation angle in the range of 0.5° to 5° before blocking the clamping assemblies by means of the locking element.

Further embodiments of the invention are set forth in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
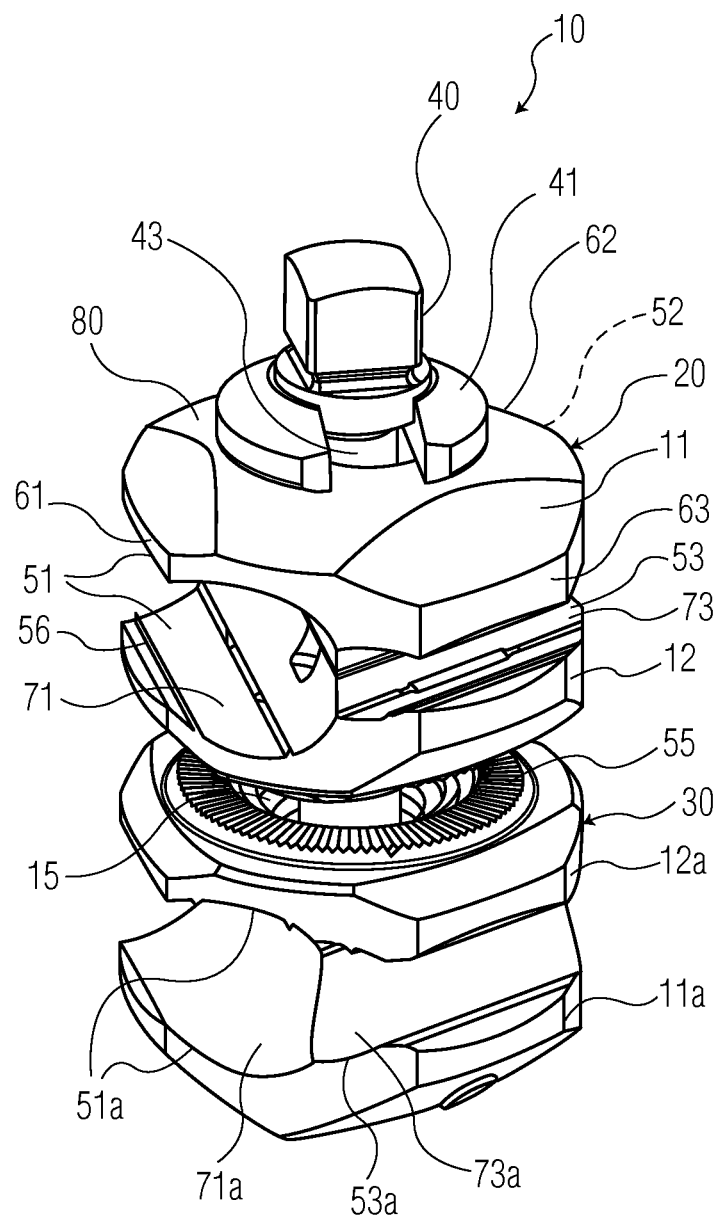
FIG. 1 shows a perspective view of a first embodiment of a fixation clamp of the present invention.
Figure 2:
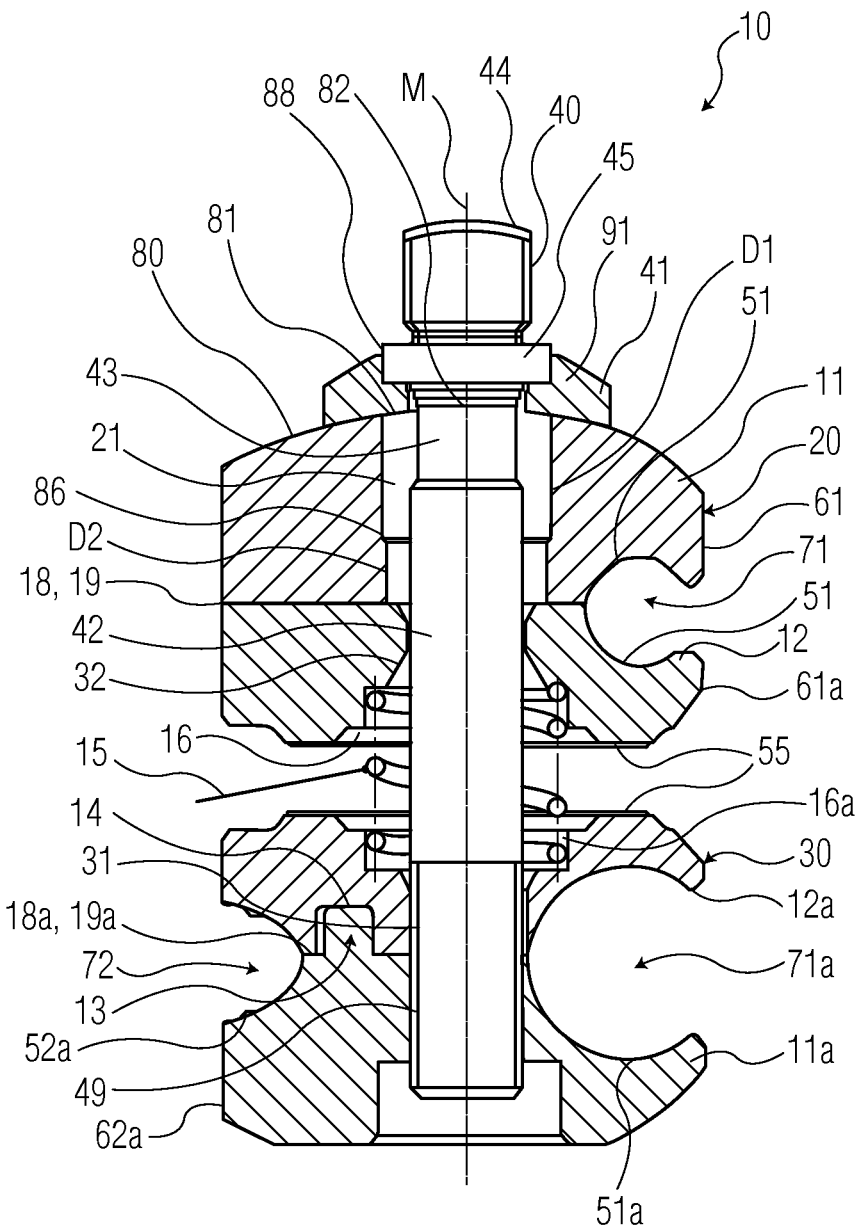
FIG. 2 shows a cross-section of the fixation clamp according to FIG. 1.

FIGS. 1 and 2 show a preferred first embodiment of a clamping element or fixation clamp 10 pursuant to the invention. The clamping element 10 consists of a first clamping assembly 20 and a second clamping assembly 30 and a locking element or shaft 40 which is positioned through bores 21, 31 within the two clamp assemblies 20, 30 along the longitudinal axis M of shaft 40. The shaft 40 is preferably a locking element adapted to allow closing the clamp assemblies 20 and 30. Shaft 40 enters a first jaw 11 through a washer 41.

The shaft 40 comprises a head portion 44, a reduced diameter portion 43 which is followed by a shaft portion 42 and a thread portion 49. The outer threaded portion 49 is adapted to be screwed into a complementary inner thread within the distal jaw 11a so that turning the head of the shaft 40 changes the longitudinal position of the shaft 40 against the lower jaw 11a, which allows opening or closing the entire clamp 10 against the force of a spring 15 provided between the two clamp assemblies 20 and 30. Spring 15 is preferably positioned in corresponding counter bores 16 and 16a in jaws 12 and 12a respectively. Instead of spring 15, provided around shaft 40, it is possible to provide a different spring means as Belleville washers or an elastic compressible solid or foam.

Upon closing of the clamp assemblies 20 and 30 the jaws 12, 12a adjacent to the spring 15 can eventually come into contact and then the anti-rotation surfaced 55 which are provided in both surfaces of the jaws 12, 12a fix the angular orientation of each clamping assembly 20 and 30 against the other.

Preferably after having mounted the shaft 40 with the thread 49 within the lower jaw 11a, the end portion of the thread 49 is destroyed through pressure to ensure that the shaft 40 cannot be removed from the clamping assemblies 20, 30 to maintain the clamp as one single piece.

Each clamping assembly 20 or 30 comprises two opposing clamping jaws 11, 12 and 11a, 12a. These jaws 11, 11a and 12, 12a are essentially similarly shaped on the sides facing each other. Each of the jaws 11, 12, and 11a, 12a comprises a respective contact surface 18, 19 and 18a, 19a facing the other surface of the jaw 11, 12 and 11a, 12a.

In order to prevent rotation between jaw 11, 11a and jaws 12, 12a as well as in order to prevent a misalignment of the jaws 11, 12 and 11a, 12a at least two orientation devices or anti-rotation devices 13, 14 is arranged on the surfaces 18a, 19a. In the present embodiment in the second clamping assembly 30 the jaw 11a comprises an opening 14 extending into surface 18 and the jaw 12a comprises a pin 13 extending from surface 19. The pin 13 extends into the opening 14. This pin-opening connection prevents therefore a possible rotation between the jaws 11a, 12a and a possible misalignment between the jaws 11a, 12a. This will further be outlined in more detail with FIGS. 5 to 11.

The jaws 11 and 12 are provided here with three grooves 51, 52 and 53. Jaws 11a, 12a have similar grooves 51a, 52a and 53a however only the grooves of jaws 11 and 12 will be described. Grooves 51, 52 and 53 are all provided in a same plane perpendicular to the longitudinal axis of shaft 40. In that plane they are oriented perpendicular to the radial direction from the center of the bore 21 or 31. As such the grooves 51, 52 and 53 are substantially parallel to outer side wall 61, 62 or 63 of each pair of jaws 11 and 12.

Each pair of grooves 51, 52 or 53, respectively, in each jaw 11 and 12, define one reception, i.e. a first reception 71, a second reception 72 and a third reception 73. The grooves 51, 52 and 53 are each formed as a rounded semi-spherical recess in section to provide receptions 71, 72 and 73 which accommodate cylindrical pins or rods with a defined diameter, if the clamp is closed. The outer side walls 61, 62 or 63 can comprise an inclined sliding surface to allow an easier clipping of such pins or rods 100 into the corresponding reception. The grooves 51, 52, 53 form rounded semi-spherical recesses in a section. This means that the recesses provided by the grooves 51, 52, 53 have a hollow cylindrical shape to accommodate rod-shaped elements. Some or all of the grooves 51, 52, and 53 are also provided with friction enhancing elements such as ribs 56.

All three grooves 51, 52 and 53 have different sizes so that the corresponding receptions 71, 72 and 73 have three different sizes. In other words each reception 71, 72 or 73 is adapted to accept a different fixation element, i.e. a rod, screw, pin or wire having a different diameter. One preferred embodiment of the first clamping assembly 20 has grooves to accept fixation elements having a diameter of 12 mm, 8 mm and 5 mm, respectively. A different embodiment may have a sequence of diameters of 8 mm, 6 mm and 4 mm, respectively.

The second clamping assembly 30 according to the embodiment of FIG. 1 also comprises two jaw portions 11a and 12a and these comprise three grooves 51a, 52a, 53a. These grooves 51, 52, 53 also comprise a sequence of different sizes. These grooves four receptions 71a, 72a and 73a having outer walls 61a, 62a and 63a. In the embodiment shown the inner jaw portions 12, 12a have an identical structure as have the outer jaws 11, 11a especially in view of the anti-rotation device 55, the counter bore 16 for a spring 15.

Within a preferred embodiment the first clamping assembly 20 may comprise a sequence of smaller sizes, e.g. 7 mm, 5 mm and 3 mm; or 6 mm, 5 mm and 4 mm; and the second clamping assembly 30 may comprise a sequence of larger sizes, e.g. 13.5 mm, 12 mm and 10 mm. Different sizes are possible, usually for wires starting from 2 mm diameter until thicker rods with a diameter of 30 mm are used within such a clamp 10. Such a clamp 10 allows using one single versatile clamp, wherein the first clamping assembly 20 is used to fix a specific pin or screw or wire having a diameter for which one of the receptions 71, 72 or 73 is adapted. The user takes the clamp 10 and orients the first clamping assembly 20 into the correct alignment so that the pin or screw can be clipped into the corresponding reception.

Then the clamp 10 can be clamped on a rod of an external fixator with the help of the second clamping assembly 30. Second clamping assembly 30 can be oriented in a way so that the rod can be clipped into the corresponding reception. It is an advantage of the clamp 10 having two clamping assemblies 20 and 30 according to the invention, that a practitioner attaching such a clamp to a bone screw with one clamping assembly 20 and subsequently a rod of an external fixator to the other clamping assembly 30 can check the robustness of his external fixator, and if he finds that the rod he has used is not stiff enough, he simply opens the second clamping assembly 30, removes the thinner rod, turns the second clamping assembly 30 e.g. 60 degrees into one direction or the other around the longitudinal axis to align the larger reception with the new thicker rod and replaces it. This change does not necessitate the replacement of the clamp 10 itself as necessary with prior art systems. The method to replace such a rod is faster and more reliable since the clamping of the bone screw is not changed, and avoids use of a second sterile clamp at said time.

It is of course also possible that the second clamping assembly 30 is a traditional clamping assembly or even any other element known in the prior art with clamping elements. The object of a versatile clamping assembly is already achieved through one first clamping assembly 20, since it allows clamping one of three different sizes of screws, pins of wires through simple reorientation of the first clamping assembly 20.

FIG. 2 shows a cross-section of the clamp according to FIG. 1, wherein the clamp 10 is shown in a premounted state, i.e. the spring 15 is under tension. The upper jaw 11 of the first clamping assembly 20 is therefore pushing the washer 41 against a flange 45 of the head of shaft 40. The bore 21 which accommodates part of the shaft portion 42 and the reduced diameter portion 43 is provided with a larger diameter than the respective diameter of the shaft 40 so that an angular or pivoting movement of the first clamping assembly 20 against the shaft 40 is possible. This is in particularly advantageous during the mounting process of the fixation clamp. With this regard it has to be noted that also bore 31 can be provided with a larger diameter than the respective section of the shaft 40 such that jaw 12 of the second clamping assembly becomes pivotable to the shaft 40.

The diameter D1, D2 of bore 21 of the first clamping assembly 20 is larger than the diameter of the locking element 40 extending through the bore 21. Thereby a pivoting movement or displacement between the locking element 40 and the first clamping assembly 20 during positioning the clamping assemblies 20, 30 and the pins or rods becomes possible. In the present embodiment the bore 21 in the first jaw 11 is a bore 21 having an abutment surface 86. The abutment surface 86 is provided by means of a step-like bore 21 having a first section with a first diameter D1 and a second section with a second diameter D2. The first diameter D1 is larger than the second diameter D2. The abutment surface 86 serves as abutment element for the locking element 40 in particular for the flange 45 in case washer 41 is removed. Hence the abutment surface 86 together with the flange 45 prevents that the first clamping assembly 20 from the second clamping assembly 30 when the washer is removed. Particularly during a cleaning or sterilization process the prevention of such a separation is very advantageous.

Alternatively the bore 21 can be provided with a conical section 32 as shown with bore 21 in the jaw 12 of the first clamping assembly. In the present embodiment there are two conical sections arranged, whereby the diameter of the bore 21 decreases with increasing length of the bore as seen from outside of the jaw 12. In case two conical sections 32 are present the degree of pivoting motion can be increased.

The shaft 40 as part of a locking element is threaded into the lower jaw 11a of the second clamping assembly 30. Hence the lower jaw 11 comprises a threaded opening. Threading may be provided in the bore or the screw may exhibit self-tapping threading. Quite generally, a locking element may be provided which may be a lever locking element or a bayonet lock. Among these locking elements may also be supporting disks or toothed disks, which, for the sake of simplicity, are not shown in the drawings.

Therefore the two clamp assemblies 20, 30 can be opened and closed through turning the head of shaft 40 and thus turning said shaft 40 in the jaw thread.

In the cross-sectional view of FIG. 2 it can also be seen that the locking element 40 extends through the first clamping assembly 20 and is in contact with the second clamping assembly 30 by means of the threaded portion 49. In mounting position in which the rods or pins will be positioned in the receptions 71, 72, 73 the first clamping assembly 20 is moveable along the middle axis M of the threaded portion 49. Upon actuation of the locking element 40 the first clamping assembly 20 will be moved against the spring pressure towards the second clamping assembly 30 such that the anti-rotation surface 55 of the first clamping assembly 20 comes into contact with the respective anti-rotation surface 55 of the second clamping assembly 30. Once the locking element 40 is firmly tightened the first clamping assembly 20 and the second clamping assembly 30 are in contact with each other via the anti-rotation surface 55.

In FIG. 2 the mounting position of clamping assemblies 20, 30 is shown. Thereby the clamping assemblies 20, 30 are positioned at the distance to each other with regard to the middle axis M. The second clamping assembly 20 is in contact with the locking element 40 and the spring 15 pushes the first clamping assembly away from the second clamping assembly 20 towards the washer 41 which is contact with the flange 45 of the locking element.

To summarize: The clamping assemblies 20, 30 will be moved due to actuation of the locking element 40 from a mounting position to a locking position and afterwards when fixation shall be cancelled from the locking position to the mounting position. After use the washer 41 will be removed as explained below in order to sterilize the clamping element 10 for further use.

Figure 3:
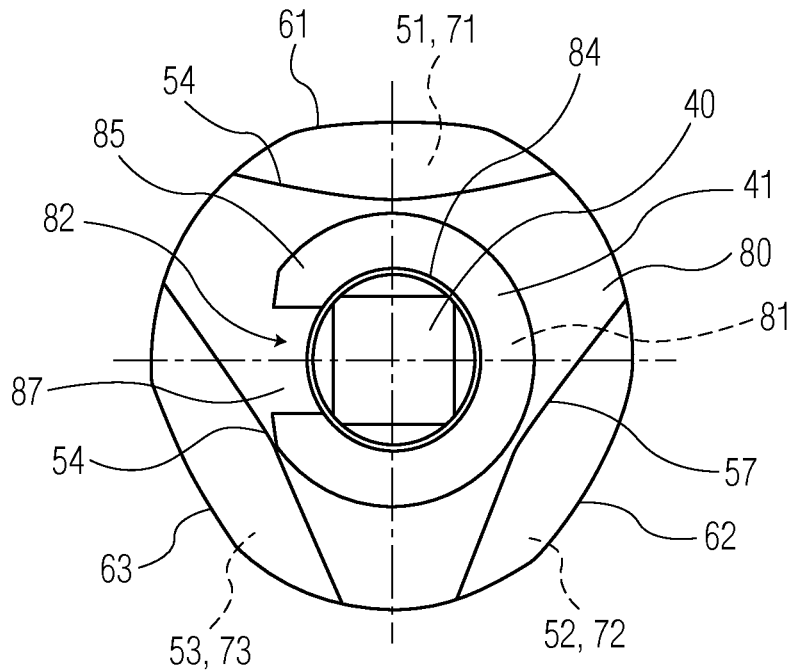
FIG. 3 shows a top view of the fixation clamp for FIG. 1.

FIG. 3 shows a view from above on the clamp according to FIGS. 1 and 2. Since the embodiment of FIG. 1 comprises three grooves 51, 52 and 53, there are three side walls 61, 62 and 63, which provide, when looked from above as in FIG. 2 a triangular shape of each clamping assembly 20 or 30.

With the aid of FIGS. 5 to 11 the at least two orientation devices or anti-rotation elements 13, 14 will now be explained in the following. While described in connection with clamping assembly 30 they may be also provided on clamping assembly 20. In principle the orientation devices serve to provide a help for the user to align a first jaw 11 with respect to a second jaw 12. Once the orientation devices 13, 14 engage with each other they also serve as anti-rotation devices to prevent unwanted rotation between the jaws 11, 12. In the following the term "orientation device" is used for the sake of simplicity.

The orientation device 13, 14 comprises an opening 14 extending into said surface 18a, 19a and a protrusion 13 extending from said surface 19a, 18a wherein said protrusion 13 engages in said opening 14. Since at least two of the orientation devices 13, 14 are arranged there are at least two protrusions 13 and at least two openings 14. Preferably the number of protrusions 13 is equal to the number of openings 14. In the present embodiment exactly two orientation devices 13, 14 are arranged.

In the present embodiment the protrusions 13 extend from the surface 18a of the first jaw 11a and the openings 14 extend from the surface 19a of the second jaw 12a into the latter. It is also possible to arrange the protrusions on the surface 19a of the second jaw 12a and the openings 14 from the surface 18a in the first jaw 11a. It is further possible to arrange one protrusion 13 and one opening 14 on/in the first jaw 11a and to arrange one protrusion 13 and one opening 14 on/in the second jaw 11a.

Figure 6:
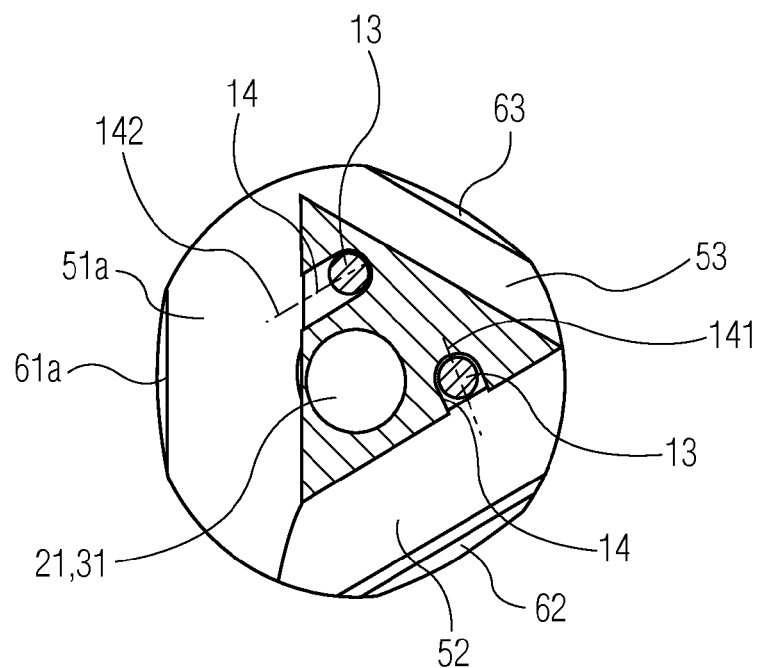
FIG. 6 shows a cross-sectional view along line X-X of FIG. 5.
Figure 10:
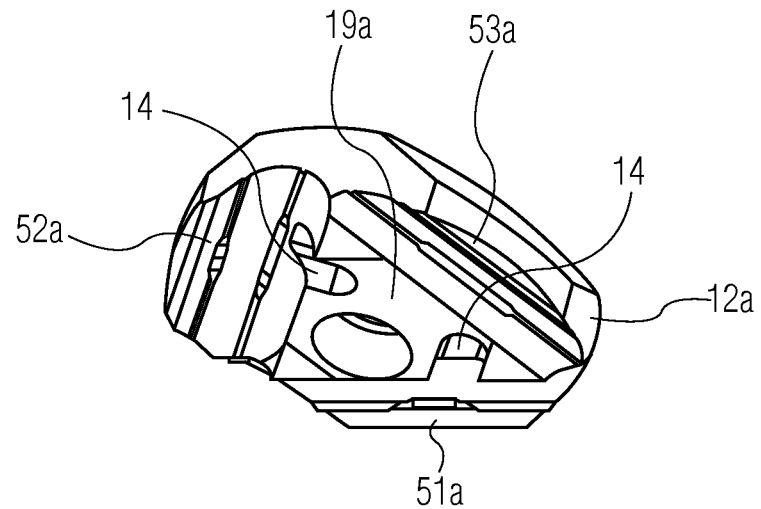
FIG. 10 shows a perspective view of a second jaw of the clamping assembly of FIG. 5.
Figure 11:
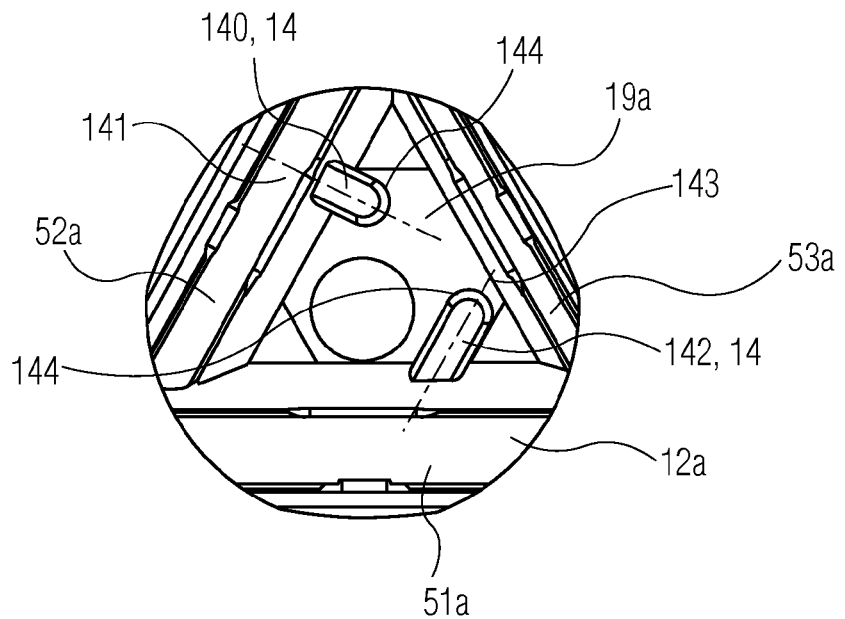
FIG. 11 shows a top view of the jaw of FIG. 10.

The openings 14 according to FIGS. 6 and 10 to 11 have the shape of channels or slots 14 extending along respective axes 140, 142. The axes 140, 142 extend substantially parallel to the plane of the contact surface from which the channels 14 extend into the jaw, here to the contact surface 19a.

The protrusions 13 have the shape of pins 13 preferably with a circular cross-section. Pins 13 then engage into channels or slots 14.

The protrusions 13 according to FIGS. 6 to 9 extends in a direction of the middle axis M of the locking element 40. The axis 140, 141 of channels 14 extends substantially perpendicular to middle axis M since the contact surfaces 18a, 19a extend also substantially perpendicular to the middle axis M. The protrusions 13 engage into channels 14 perpendicular to said axis 140, 141 of the channels 14.

In the present embodiment there are arranged at least two, (exactly two are shown), channels 14. A first channel 140 extends along a first axis 141 being substantially parallel to surface 19a and a second channel 142 extends along a second axis 143 being substantially parallel to surface 19a. The first axis 141 is arranged angularly to second axis 143. Preferably the angle between the first axis 141 and the second axis is in the range of 60 to 120°, more preferably the angle is substantially a right angle of 90°.

The first axis 141 or the channel 140 extend substantially perpendicular to the direction of a neighboring groove 51a. The term direction of a groove is to be understood as the direction of a middle axis that extends along the groove.

The second axis 143 or the channel 142 extends angular, preferably with an angle in the range of 30° to 60°, in particular with an angle of 45°, to the direction of a neighboring groove 51a.

Figure 6A:
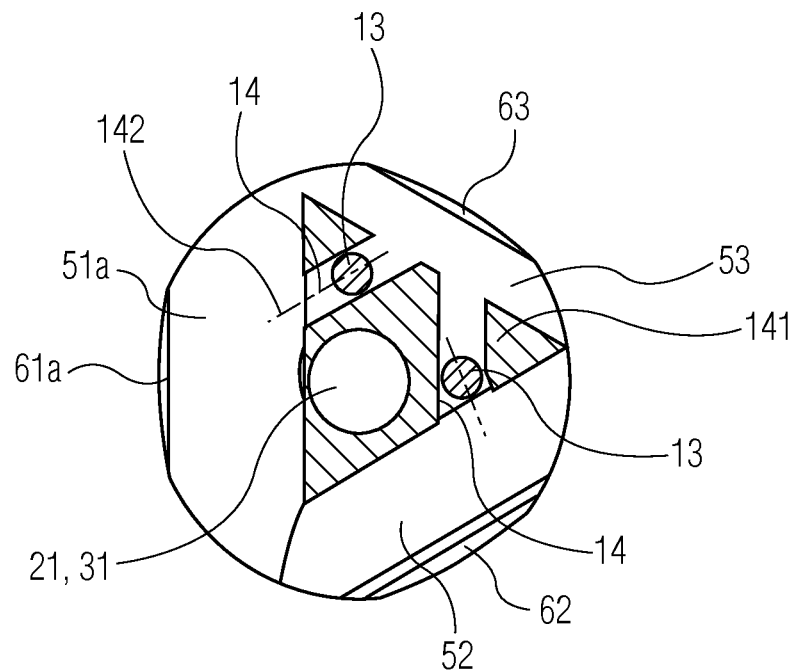
FIG. 6A is the cross-sectional view of FIG. 6 showing an alternate slot or channel design.
Figure 7:
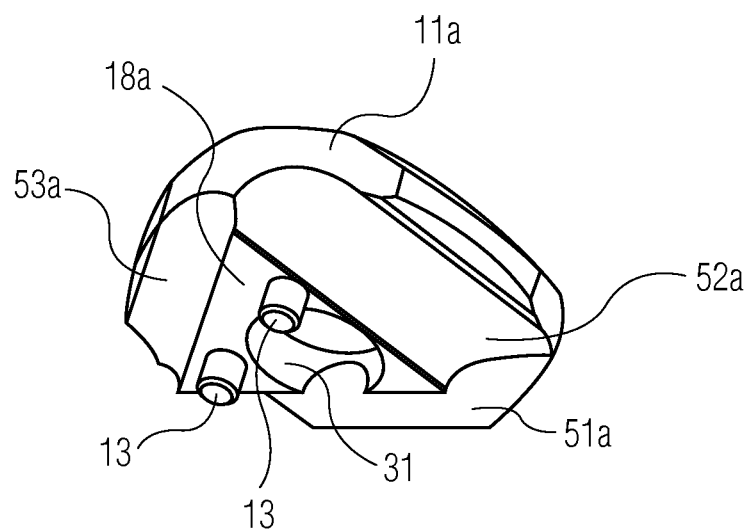
FIG. 7 shows a perspective view of a first jaw of the clamping assembly of FIG. 5.
Figure 8:
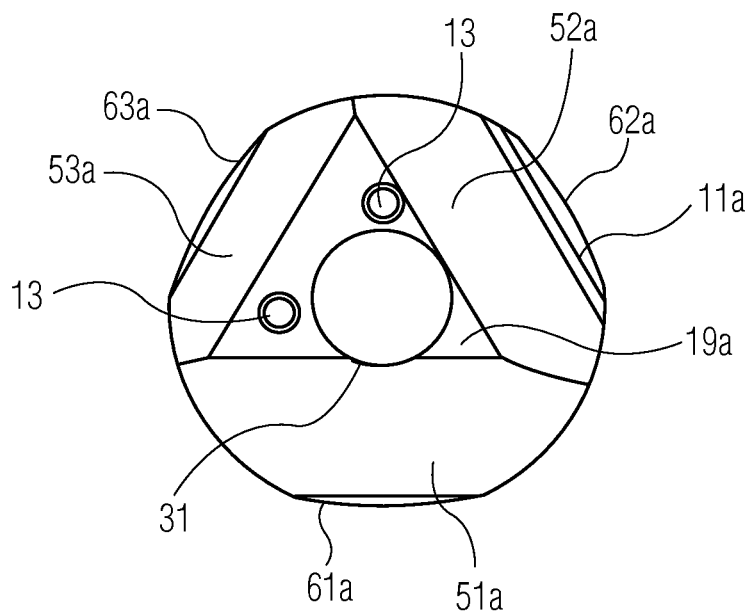
FIG. 8 shows a top view of the jaw of FIG. 7.
Figure 9:
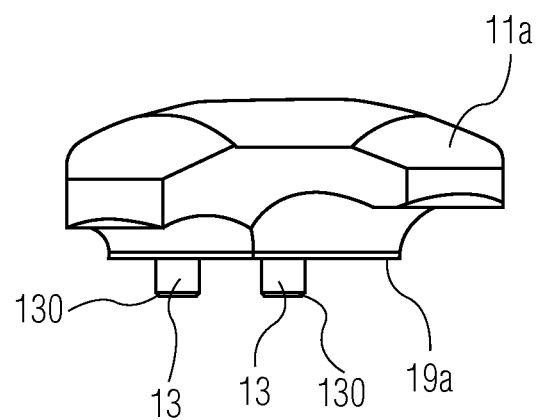
FIG. 9 shows a side view of the jaw of FIG. 7.
Figure 10A:
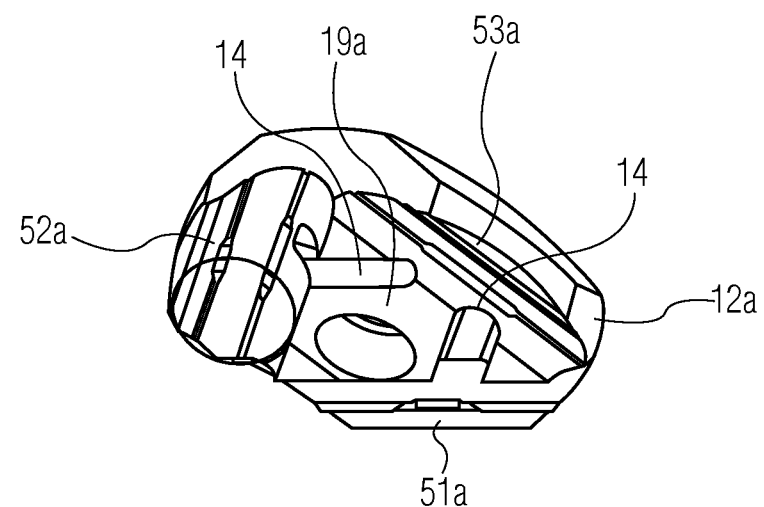
FIG. 10A is the perspective view of FIG. 10 showing the alternate slot or channel design of FIG. 6A.
Figure 11A:
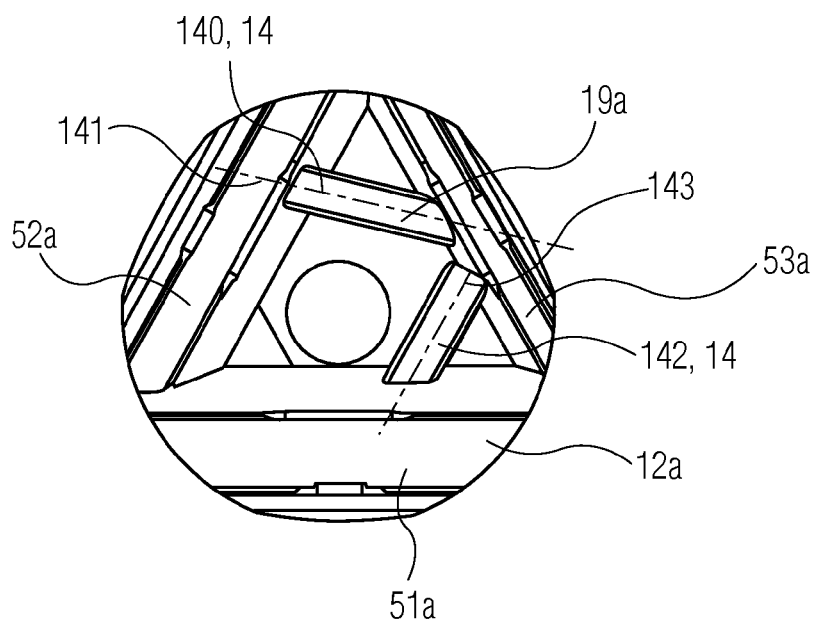
FIG. 11A is the top view of FIG. 11 showing the alternate slot or channel designs of FIGS. 6A and 10A.

At least one of the channels, here both channels 140, 142 open out into a neighboring groove 51a, 52a and are limited on the opposite side of the groove 51a, 52a as viewed along the respective axis 140, 142 preferably by an abutment element 144. In other embodiments as shown in FIGS. 6A, 10A and 11A, it may also be possible to omit the abutment element such that a channel is provided which extends from a first groove to a second groove. Hence such a channel then opens out in two grooves. However, the abutment element 144 has advantages in view of the accuracy of the orientation between the jaws 11a, 12a. Nevertheless it has to be noted that an open channel 140, 142, even if it is open on one end only has advantages concerning the sterilization process as the fluid enters the channel also via grooves 51a, 52a.

The abutment element 114 has a surface which is preferably curved around a middle axis extending perpendicular to the respective surface 18a, 19a.

With regard to the arrangement of the pins 13 and the channels 14 it has to be mentioned that they are arranged such that the first jaw 11a and the second jaw 12a are connectable in only one determined aligned position such that a misalignment becomes impossible.

Furthermore the orientation devices 13, 14 are provided such that rotation of the first jaw 11a with respect to the second jaw 12a is prevented.

Alternatively the orientation devices 13, 14 are provided such that rotation of the first jaw 11a with respect to the second jaw 12a is permitted in a narrow field of rotation. A narrow field of rotation can be defined as a rotation angle in the range of 0.5° to 5°. However such a rotation shall only be permitted during the mounting process of the fixation clamp, i.e. before blocking said clamping assemblies 20, 30 by means of the locking element 40. In order to allow such a rotation, the channels 14 and pins 13 are provided with respective tolerances. Hence the channel 14 can be provided with a larger width such that the pin 13 is able to move with respect to the channel 14. The pin 13 then abuts at the sidewalls limiting the channel 14. The sidewall are the walls limiting the channel this extending from the surface 18a, 19a into the jaw.

The depth of the opening 14 from the surface 18a, 19a along the middle axis M of the locking element is preferably larger than the length of the protrusion 13 in the same direction. This configuration ensures that the surfaces 18a, 19a are always in full contact with each other.

The protrusion 13 can also be provided with a chamfered edge 130 allowing a better insertion of the protrusion into the opening.

Furthermore the orientation device 13, 14 allows better positioning of the jaws 11a, 12a with respect to each other. In particular the jaws may move slightly in a floating manner with respect to each other which enables a self-centering function once the pin or rod has been introduced into the respective reception 71a, 72a, 73a.

Reference is now made to FIGS. 1 to 4. In the present embodiment the first clamping assembly 20, here jaw 11, comprises a first contact surface 80 which is in contact with a second contact surface 81 of the washer 41. The washer 41 and the first clamping assembly 20 are in contact via contact surfaces 80, 81. The contact surfaces 80, 81 are spherical having the same curvature radius such that the washer 41 is enabled to slide with respect to the first clamping assembly 20 on the contact surface 80 when it comes to the above mentioned pivoting motion of the first clamping assembly 20 with respect to the locking element 40. The curvature is at least the same over an overlapping surface which here is defined as the surface which encompasses the maximal gliding motion of the washer 41 on the contact surface 80.

In the present embodiment the first contact surface 80 has a convex shape, whereas the second contact surface 81 has a concave shape. Such a configuration is particularly advantageous as it allows a pivoting motion as mentioned above while providing a very compact structure of the fixation clamp in terms of axial and radial dimension. Furthermore the surfaces which are shaped as explained allow that the washer 41 as explained in detail below is removable from the clamping element 10. Thereby the first clamping assembly 20 and the second clamping assembly 30 become loose such that the parts are slightly moveable along middle axis M and sterilization of the clamping element 10 is possible without demounting or disassembling the clamping element 10 completely. This is very advantageous since during sterilization the parts remain together and re-assembly of the parts afterwards is not necessary. Hence the parts of the clamping element 10 remain loosely together such that the sterilization fluid is able to enter clearances between the respective parts. As mentioned above providing the diameters D1 and D2 accordingly, the abutment surface 86 serves as element which holds the parts loosely together.

The first contact surface 80 of the first clamping assembly 20 extends from a section point 82 between the middle axis M of the locking element 40 and said first contact surface 80 towards the first clamping assembly 20.

FIG. 3 shows the clamping element from above. In FIG. 3 the overlapping surface with limiting edges 54 can be recognized.

Figure 4:
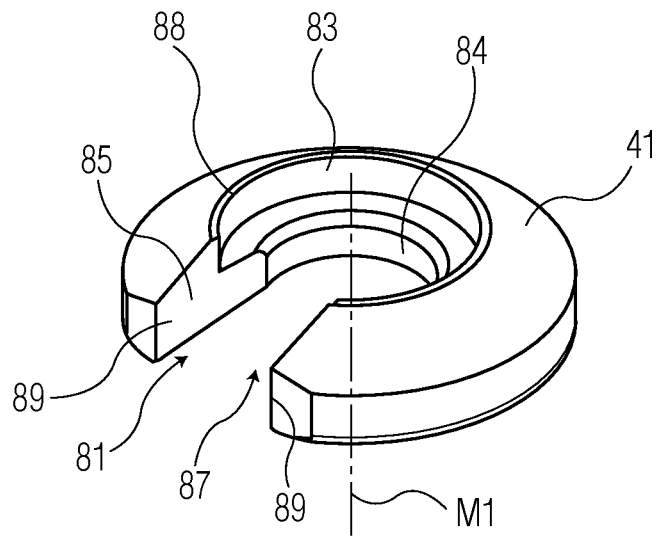
FIG. 4 shows a perspective view of a washer that is used in the fixation clamp of FIG. 1.
Figure 5:
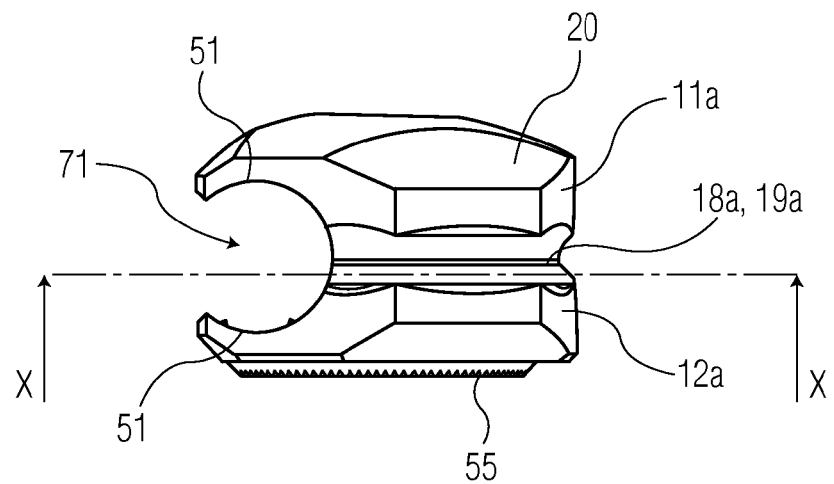
FIG. 5 shows a side view of a clamping assembly of the clamping element of FIG. 1.

FIG. 4 shows the washer 41 in a perspective view and in FIG. 2 a cross-sectional view of the washer 41 is shown. In the following the structure of the washer 41 will be explained.

The washer 41 comprises as mentioned above the contact surface 81 and an upper surface 88 which is arranged at a distance from the contact surface 81. A central through opening 84 having a middle axis M1 that is at least partly circumvented by means of a sidewall 85. Said through opening extends from contact surface 81 to the upper surface 88. The locking element 40 extends through the through opening.

The sidewall 85 is interrupted by cutout 87 which extends radially to the middle axis M1 through the sidewall 85 to the opening 84 such that the sidewall 85 becomes interrupted. The cutout 87 has a width which is slightly larger than the reduced diameter portion 43 of the locking element 40 such that the washer 41 can be moved radially to the locking element 40 in order to remove the washer 41 after the use of the clamping element 10. The width is defined as the clearance of the cutout 87 from the surfaces 89 of the sidewall limiting the cutout.

Furthermore the washer 41 comprises a recess 83 extending along middle axis M1 from an upper surface 88 which is arranged opposite the contact surface 81. The recess 83 is designed to accommodate the flange 45 of the locking element 40. The recess 83 can also be designated as abutment element since it prevents the washer from being radially displaced to the middle axis M of the locking element 40. In order to demount the washer 41 it is necessary to push the first clamping assembly 10 towards the second clamping assembly, such the washer 41 can also be moved along the middle axis M of the locking element 40. Thereby the flange 45 will be moved out of the recess 83. Once the flange 45 has been moved such that there is no connection between the flange 45 and the recess 83, the washer 41 can be moved radially to the locking element 40 whereby the shaft of the locking element will pass the cutout 87 of the washer.

Recess 83 extends from the upper surface 88 along the middle axis M1 of the through opening 84 into the washer 41. The washer is preferably made out of a metallic material.

To summarize the arrangement of the contact surfaces 80, 81 has the advantage that during the mounting process of the fixation clamp 10 a pivoting motion of the first clamping assembly becomes possible with a large deflection. Furthermore the removable washer 41 has the advantage that the clamping assemblies 20, 30 become moveable along the interlocking element 40 such that an effective sterilization becomes possible.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation clamp for use in an external fixation system for holding bone fragments adjacent to each other with the help of fixation elements, said fixation clamp comprising:
   at least one clamping assembly comprising first and second jaws, and
   at least one locking element having a central longitudinal axis extending through the first and second jaws for blocking the first and second jaws;
   the first jaw having a first contact surface and a first, second and third groove; the second jaw having a first contact surface and a first, second and third groove, the second jaw first contact surface is in contact with the first contact surface of the first jaw;
   three receptions are provided by the alignment of the first, second and third grooves on the first and second jaws, each reception can accommodate a fixation element along a longitudinal axis of the respective reception;
   first and second orientation devices that extend from and/or into said first contact surfaces of the first and second jaw, the first and second orientation devices are adapted to orient the first jaw with respect to the second jaw, wherein the first orientation device comprises an elongate recess extending from said first contact surfaces into the first jaw and the second orientation device comprises a protrusion extending from the first contact surfaces of the second jaw, wherein said protrusion engages in said elongate recess, wherein the elongate recess has the shape of a channel or a slot extending along a first central longitudinal axis which is substantially parallel to a plane of the first jaw first contact surface wherein the protrusion extends in a direction parallel to the central longitudinal axis of the locking element and said first central longitudinal axis of said channel or slot extends in a plane substantially perpendicular to said central longitudinal axis of the locking element, wherein said protrusion engages into said channel or slot in a direction perpendicular to said central axis of the channel or slot and wherein said channel or slot opens out into two of the first, second and third grooves.

2. The fixation clamp according to claim 1, wherein the elongate recess comprises a first channel or slot extending along the first central longitudinal axis being parallel to said first contact surface of the first jaw further comprising a second channel or slot extending along a second central longitudinal axis being parallel to said first contact surface of the first jaw, wherein the first central longitudinal axis is angularly arranged to said second central longitudinal axis so that the first channel or slot extends between the first and second grooves and the second channel or slot extending between the first and third grooves.

3. The fixation clamp according to claim 2, wherein the first central longitudinal axis of the first channel or slot extends substantially perpendicular to the direction of the first groove.

4. The fixation clamp according to claim 2, wherein the second central longitudinal axis of the second channel or slot extends at an angle in the range of 30° to 60° to the direction of the first groove.

5. The fixation clamp according to claim 2, wherein the first axis of the first channel or slot and the second axis of the second channel or slot extend at an angle of 60° to 120° to each other.

6. The fixation clamp according to claim 2, wherein the second jaw comprises first and second protrusions for engaging the first and second channel or slot respectively, each protrusion having the shape of a pins with a circular cross-section.

7. The fixation clamp according to claim 6, wherein the first and second protrusions and the first and second channels or slots are arranged such that the first jaw and the second jaw are connectable in only one determined aligned position.

8. The fixation clamp according to claim 1, wherein the orientation devices are provided such that rotation of the first jaw with respect to the second jaw is prevented or wherein the orientation devices are provided such that the angular rotation between the first jaw and the second jaw is permitted at a rotation angle between 0.5° to 5° before blocking the first and second jaws by means of the locking element.

9. The fixation clamp according to claim 1, wherein a washer is arranged between said locking element and the first jaw and wherein said first jaw comprises a second contact surface which is spherical and convex and in that said washer comprises a contact surface which is spherical and concave, wherein the first jaw second contact surface is in contact with the washer contact surface.

10. The fixation clamp according to claim 1, wherein the first and second jaws comprise a bore through which said locking element extends, wherein said bore comprises a diameter that is larger than the diameter of the locking element, wherein the first and second jaws are pivotable with respect to the locking element.

11. A fixation clamp for an external fixation system comprising:
a first and a second jaw member respectively having first and second facing contact surfaces each including a first, a second and a third groove angled with respect to one another, and the first and second jaw members having alignable through bores;
a locking element extending through the bores in the first and second jaw members and the first and second contact surfaces, the locking element capable of blocking the first and second contact surfaces against one another;
means for moving the first and second contact surfaces along the shaft towards one another; and
first and second recessed openings formed in the first jaw member, each recessed opening open to the first contact surface and first and second protrusions on the second jaw member extending outwardly from the second contact surface and movable into the respective first and second recessed opening by said means for moving the first and second contact surfaces towards one another wherein the first recessed opening is a channel or slot that extends completely along a linear first axis and opens out into the first and second grooves, and the second recessed opening has the shape of a channel or slot that extends completely along a linear second axis and opens out into the first and third grooves, wherein the first axis extends at an angle to said second axis and wherein the first axis and the second axis extend angularly with an angle of 60° to 120° to each other.

12. The fixation clamp according to claim 11 wherein the protrusions and respective channels or slots engage such that rotation of the first jaw member with respect to the second jaw member is permitted between a rotation angle of 0.5° to 5° before blocking said first and second jaw by means of the locking element.

13. A fixation clamp for use in an external fixation system for holding bone fragments adjacent to each other with the help of fixation elements, said fixation clamp comprising:
at least one clamping assembly having a bore therethrough, and
at least one locking element extending through the bore of the at least one clamping assembly for blocking the position of the at least one clamping assembly in a defined angular position;
wherein said clamping assembly comprising:
a first jaw having a first contact surface with first, second and third grooves;
a second jaw having a first contact surface with first, second and third grooves, the second jaw first contact surface is adjacent the first contact surface of the first jaw, when the first, second and third grooves on the first and second jaws are aligned;
three receptions are provided by the alignment of said first, second and third grooves of the first and second jaws to accommodate a fixation element along a longitudinal axis of the reception;
two first orientation devices are provided on the first jaw and two second orientation devices are provided on the second jaw that extend from and/or into the respective first contact surfaces, the two first and two second orientation devices are adapted to orient the first jaw with respect to the second jaw and wherein the two first and two second orientation devices are provided such that a rotation angle of the first jaw with respect to the second jaw is only permitted in the range of 0.5° to 5° before locking said clamping assemblies by means of the locking element wherein the two first orientation devices are elongate slots respectively extending between and opening into the first and second grooves and into the first and third grooves, which slots includes a surface for respectively engaging the two second orientation device to limit the rotation angle to 0.5° to 5°; and
wherein the two first orientation devices elongate slots each extends along a linear axis which is substantially parallel to the first jaw first contact surface.

14. The fixation clamp according to claim 13, wherein between said locking element and said at least one clamping assembly there is arranged a washer and wherein, one of said first and second jaws comprises a second contact surface which is spherical and convex and wherein said washer comprises a first contact surface which is spherical and concave, wherein the jaw second contact surface is in contact with the washer first contact surface.

15. The fixation clamp according to claim 13, wherein the clamping assembly comprises a bore through which said locking element extends, wherein said bore comprises a diameter that is larger than the diameter of the locking element allowing the clamping assembly to pivot against the locking element.

* * * * *